United States Patent
Agisim et al.

(10) Patent No.: US 9,308,166 B2
(45) Date of Patent: Apr. 12, 2016

(54) ENHANCED STABILITY OF NOVEL LIQUID COMPOSITIONS

(71) Applicant: Pfizer Inc, New York, NY (US)

(72) Inventors: Gary Robert Agisim, Henrico, VA (US); Robert Alan Friedline, Midlothian, VA (US); Shivangi Akash Patel, Mechanicsville, VA (US); César Iván Sertzen, Richmond, VA (US); Vanessa Rose Shepperson, Powhatan, VA (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 14/192,720

(22) Filed: Feb. 27, 2014

(65) Prior Publication Data

US 2014/0243364 A1 Aug. 28, 2014

Related U.S. Application Data

(60) Provisional application No. 61/770,988, filed on Feb. 28, 2013.

(51) Int. Cl.

| A61K 31/135 | (2006.01) |
|---|---|
| A61K 31/44 | (2006.01) |
| A61K 9/08 | (2006.01) |
| A61K 31/09 | (2006.01) |
| A61K 31/137 | (2006.01) |
| A61K 31/485 | (2006.01) |
| A61K 47/10 | (2006.01) |
| A61K 9/48 | (2006.01) |
| A61K 45/06 | (2006.01) |
| A61K 9/00 | (2006.01) |

(52) U.S. Cl.
CPC ............... *A61K 9/08* (2013.01); *A61K 9/0095* (2013.01); *A61K 9/4866* (2013.01); *A61K 31/09* (2013.01); *A61K 31/137* (2013.01); *A61K 31/485* (2013.01); *A61K 45/06* (2013.01); *A61K 47/10* (2013.01)

(58) Field of Classification Search
CPC ... A61K 31/09; A61K 31/137; A61K 31/485; A61K 47/10; A61K 9/0095; A61K 9/08; A61K 9/4866
USPC .................................................. 514/289, 653
See application file for complete search history.

(56) References Cited

U.S. PATENT DOCUMENTS

| 4,522,828 A | 6/1985 | Jeffery et al. |
|---|---|---|
| 5,196,436 A * | 3/1993 | Smith ............................ 514/289 |
| 5,484,606 A | 1/1996 | Dhabhar |
| 5,505,961 A | 4/1996 | Shelley et al. |
| 8,318,210 B2 * | 11/2012 | Tengler et al. ................ 424/501 |
| 2008/0014261 A1 | 1/2008 | Giordano et al. |
| 2008/0085892 A1 | 4/2008 | Kandeepan et al. |
| 2013/0084340 A1 * | 4/2013 | Tengler et al. ................ 424/492 |

FOREIGN PATENT DOCUMENTS

| WO | WO9300072 | 1/1993 |
|---|---|---|
| WO | WO9519759 | 7/1995 |
| WO | WO9523595 | 9/1995 |
| WO | WO9702273 | 1/1997 |

OTHER PUBLICATIONS

Anderson et al., "Excipients for Oral Liquid Formulations", Jul. 2006, Book: "Excipient Development for Pharmaceutical, Biotechnology, and Drug Delivery Systems", Edited by Ashok Katdare and Mahesh V. Chaubal, Chapter 11, pp. 155-180.*
International Search Report.
Mani, N., et al., "Solubility of Guaifenesin in the Presence of Common Pharmaceutical Additives", Pharmaceutical Development and Technology, 2003, pp. 385-396, vol. 8, No. 4.

* cited by examiner

*Primary Examiner* — My-Chau T Tran
(74) *Attorney, Agent, or Firm* — Jeffrey M. Gold; Paula K. Davis

(57) ABSTRACT

The present invention relates to compositions of pharmaceutical agents in combination with additional pharmaceutical agents in a mixture of polyethylene glycol, polyvinylpyrrolidone, and propylene glycol and a process of making the compositions.

6 Claims, No Drawings

ENHANCED STABILITY OF NOVEL LIQUID COMPOSITIONS

This application claims the benefit under 35 USC 119(e) of U.S. Provisional Application No. 61/770,988 filed on Feb. 28, 2013, the contents of which is hereby incorporated by reference in its entirety.

FIELD OF INVENTION

The present invention relates to compositions and a process whereby the composition comprises pharmaceutical agents alone or in combination with additional pharmaceutical agents in a mixture of polyethylene glycol, polyvinylpyrrolidone (PVP) and propylene glycol.

BACKGROUND OF THE INVENTION

Liquid, and especially concentrated liquid, pharmaceutical compositions offer several advantages over solid compositions. Liquids are easy to swallow and provide an excellent vehicle for the uniform delivery of pharmaceutical agents. Moreover, liquids provide a rapid onset of pharmacologic action, since the composition does not first have to disintegrate and dissolve in the gastrointestinal tract. Likewise, concentrated liquid compositions offer certain distinct advantages, such as faster onset of efficacy due to the high concentration of pharmaceutical agents. Consumers prefer a concentrated liquid composition due to the ease of dosing, and less volume of doses.

These advantages notwithstanding, it is, however, often difficult to prepare such compositions using the desired pharmaceutical agents. Many pharmaceutical agents are poorly soluble and, therefore, require relatively large volumes of solvent for dissolution, resulting in impractically large doses. Furthermore, the situation becomes even more complicated when multiple pharmaceutical agents are involved, and particularly where the soluble pharmaceutical agent is in combination with additional water soluble pharmaceutical agent(s) that may hinder the efficacy of at least one or more of the pharmaceutical agents and produce a bitter taste that consumers would be discouraged from using.

Guaifenesin is a well known pharmaceutical agent, classified as an expectorant, and is sold as tablets or syrups under many brand names. Single-ingredient formulations of guaifenesin are available, and it is also included in many other over-the-counter cough and cold remedy combinations, usually in conjunction with dextromethorphan and/or acetominophen and/or ephedrine/pseudoephedrine or phenylephrine. Guaifenesin is a component of Robitussin™ DM, Robitussin™ DM MAX, Robitussin™ CF Max and other well known brand names. Generally the concentration of guaifenesin in most over-the-counter cough medicines is approximately 100 mg/5 mL liquid to 200 mg/5 mL. As an example, the Robitussin™ CF Max product contains 100 mg/5 mL and Mucinex™ Fast-Max™ Severe Congestion and Cough product contains 100 mg guaifenesin/5 mL liquid.

It has been reported in the literature that the aqueous solubility of guaifenesin, a soluble drug in water, could be significantly reduced in the presence of salts, sugars, and higher concentrations of cosolvents. See "Solubility of Guaifenesin In The Presence Of Common Pharmaceutical Additives," Narasimhan Mani, Pharm Dev Technol 8:385-96. 2003.

Many commercially available over-the-counter liquid cold, cough, flu, fever, and/or allergy preparations contain pseudoephedrine as an active agent. Although such preparations have been useful, misuse of such products as a starting material for synthesis of illicit substances has lead to the desire to find alternatives that are not suitable for such illicit synthesis. Phenylephrine is a potential alternative agent. However, phenylephrine is susceptible to degradation. The degradation is typically facilitated in excipient compositions of the type typically used with pseudoephedrine.

Accordingly, it would be desirable to have a palatable, stable, liquid composition with inhibited precipitation of pharmaceutical agents, such as guaifenesin, alone or in combination with additional pharmaceutical agents, such as phenylephrine, in a mixture of polyethylene glycol, polyvinylpyrrolidone and propylene glycol.

SUMMARY OF THE INVENTION

In one embodiment, the present invention relates to an oral liquid composition comprising:
i.) from about 0.1% to about 20% w/v polyvinylpyrrolidone;
ii.) from about 5% to about 70% w/v polyethylene glycol;
iii.) from about 1% to about 30% w/v propylene glycol;
iv.) from about 1% to 10% w/v guaifenesin; and
v.) from about 0.01% to about 1.0% w/v phenylephrine.

In another embodiment, the present invention relates to a liquid oral pharmaceutical composition comprising:
i.) about 0.2% w/v dextromethorphan;
ii.) about 4% w/v guaifenesin;
iii.) about 0.1% w/v phenylephrine;
iv.) about 10% w/v propylene glycol;
v.) about 10% w/v polyethylene glycol; and
vi.) about 0.5% w/v polyvinylpyrrolidone.

The composition may be a solution or a suspension. In some embodiments the composition may be filled into capsules.

The present invention further relates to a process for preparing an oral liquid composition, comprising the steps of:
a.) mixing until dissolved from about 0.1% to about 20% w/v of polyvinylpyrrolidone in an aqueous phase;
b.) adding and mixing from about 1% to about 20% w/v of at least one pharmaceutical agent;
c.) subsequently adding and mixing:
  i.) water;
  ii.) from about 1% to about 30% w/v of a propylene glycol;
  iii.) from about 5% to about 70% w/v of a polyethylene glycol; and
d.) subsequently adding and mixing one or more additional ingredients.

DETAILED DESCRIPTION OF THE INVENTION

The present invention provides a palatable, stable, oral liquid composition with inhibited precipitation of pharmaceutical agents, such as guaifenesin, in combination with additional pharmaceutical agents, such as phenylephrine, in a mixture of polyethylene glycol, polyvinylpyrrolidone (PVP) and propylene glycol. The composition is particularly well suited for the relief of cold, cough, flu, fever, headache, pain, body ache, migraine, and allergy symptoms.

The composition of the invention may be a solution or a suspension or alternatively filled into capsules. In solution and suspension embodiments, the composition comprises guaifenesin and phenylephrine, in a mixture of polyethylene glycol, polyvinylpyrrolidone and propylene glycol. Optionally, the composition may comprise one or more other agents.

"Solution" as used herein means a uniform dispersed mixture at molecular or ionic level of one or more pharmaceutical actives (the solute) in one or more other substances (the solvent). The physical state of the solution at normal ambient conditions is such that it is readily dispensed from a vessel by pouring.

Consumers show strong preference for lower dose volumes that contain a sufficiently high enough concentration of pharmaceutical actives to provide the desired therapeutic benefit of the active. As a result of this effort to meet consumer needs, the compositions of the present invention are intended to be dosed in low volumes.

Method for Delivery of the Composition into the Body

The delivery of drugs into the bloodstream by placing a dosage form into the mouth can be classified into two major subclasses dependent upon the desired action. In one case where the drug is delivered into the blood by absorption after swallowing (i.e. from the stomach, small intestine or colon) and in the other case where absorption, or at least the significant amount of the absorption occurs through the membranes of the oral cavity either immediately or over extended periods of time when the compositions are retained in the mouth prior to swallowing. This route is generally referred to as "buccal" or "oral mucosal" absorption versus the former route normally referred to as peroral administration of actives. Peroral administration of actives is by far the most commonly used in all of medicine, has been well studied, and is explained in detail in: Mayerson, M., Principles of Drug Absorption; Chapter 2 in "Modem Pharmaceutics", 2nd ed., G. S. Banker and C. T. Rhodes, editors, Marcel Dekker Inc., New York, 1990; herein incorporated by reference.

The preferred route of administration of the present invention is peroral.

All percentages and ratios used herein are by weight per volume (% w/v) and all measurements are at 25° C., unless otherwise indicated.

Liquid Pharmaceutical Compositions

The liquid pharmaceutical compositions of the present invention comprise the following components, as well as optional components.

Polyethylene Glycol (PEG)

A component of the present compositions is a polyethylene glycol. Polyethylene glycols generally are clear, viscous liquids or white solids which are soluble in water and many organic solvents. Polyethylene glycols are generally bitter tasting, especially the lower molecular weight glycols, which are usually the most effective glycols in solubilizing pharmaceutical agents. These polymers correspond to the general formula:

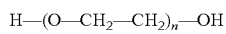

where n is greater than or equal to 4.

Polyethylene glycols are described in G. M. Powell, III in Handbook of Water-Soluble Gums & Resins, R. L. Davidson, Ed. (McGraw-Hill, New York, 1980) pp. 18/1-18/31, this reference being incorporated herein by reference in its entirety. Polyethylene glycols, which are also known as "PEGs" or "polyoxyethylenes", are designated by both their average molecular weight range and their average "n" value as in the above designated formula. For example, polyethylene glycol 400, which is also known by the CTFA designation, PEG-8, has an average molecular weight range from 380-420 and an average value of n between 8.2 and 9.1. See CTFA Cosmetic Ingredient Dictionary, Third Edition (1982), pp. 201-203; and The Merck Index, Tenth Edition, entry 7441, p. 1092 (1983); these two references being incorporated herein by reference in their entirety.

The polyethylene glycols useful herein are mixtures of those which are liquids at room temperature or have a melting point slightly there above. Preferred mixtures include those polyethylene glycols having a molecular weight range of from about 300 to about 1500 and corresponding n values of from about 6 to about 30. More preferred are those of polyethylene glycols having a molecular weight range of from about 400 to about 800 and corresponding n values of n from about 8 to about 16. Most preferred are those polyethylene glycols having a molecular weight range of from about 400 to about 600 and corresponding n values from about 8 to about 12. Liquid and low-melting polyethylene glycols are commercially available from multiple sources, including Sasol GmbH of Hamburg, Germany and Union Carbide (Danbury, Conn.) under the Carbowax™ trademark. See "Carbowax™ Polyethylene Glycols", Union Carbide Technical Bulletin f-4772M-ICD 11/86-20M, this reference being incorporated herein by reference in its entirety.

The oral liquid compositions of the present invention comprise from about 5% to about 70% w/v polyethylene glycol, more preferably from about 7% to about 30% w/v, and most preferably about 10% w/v polyethylene glycol. The process for making the oral liquid compositions of the present invention include the addition of polyethylene glycol within the stated ranges above.

Polyvinylpyrrolidone (PVP)

A component of the present compositions is polyvinylpyrrolidone, which is a polymer of N-vinyl-2-pyrrolidone.

Polyvinylpyrrolidones are described in L. Blecher et al. in Handbook of Water-Soluble Gums & Resins, R. L. Davidson, Ed. (McGraw-Hill, New York, 1980) pp. 21/1-21/21, this reference being incorporated herein by reference in its entirety. Polyvinylpyrrolidone has different solubility characteristics based on its polymeric structure. Long-chain polyvinylpyrrolidone, which is also known as povidone, has good solubility in water and a number of organic solvents. Cross-linked polyvinylpyrrolidone, which is also known as crospovidone, is insoluble in virtually all common solvents. Both the soluble and insoluble forms of polyvinylpyrrolidone are commercially available from GAF Chemicals Company (Wayne, N.J.) under the Plasdone™ and Polyplasdone™ trademarks, respectively, and from BASF Aktiengesellschaft (Ludwigshafen, Germany) under the Kollidon™ trademark. Soluble forms of polyvinylpyrrolidone include Plasdone™ K-25, Plasdone™ K-26/28, Plasdone™ K-29/32, PlasdoneV C-15, Plasdone™ C-30, Plasdone™ C-90, Kollidon™ 12 PF, Kollidon™ 17 PF, Kollidon™ 25, Kollidon™ 30, and Kollidon™ 90 Grades, Polyvinylpyrrolidone for the Pharmaceutical Industry", BASF Technical Bulletin MEF 129e, Register 2, May 1986 (Bn); these references being incorporated herein by reference in their entirety.

The soluble forms of polyvinylpyrrolidone are preferred for use in the present invention. Preferred are soluble polyvinylpyrrolidones having an average molecular weight in the range of from about 2,000 to about 1,500,000; more preferred are those having an average molecular weight in the range of about 1,000,000 to about 1,500,000. Moreover, mixtures of two or more soluble polyvinylpyrrolidones of different average molecular weight can be employed. Kollidon™ 90 grade is the preferred grade of polyvinylpyrrolidone utilized in the present invention.

The oral liquid compositions of the present invention comprise from about 0.1% to about 20% w/v of a soluble polyvinylpyrrolidone, more preferably from about 0.20% to about 2% w/v, and most preferably about 0.5% w/v polyvinylpyrrolidone. The process for making the oral liquid compositions of the present invention include the addition of polyvinylpyrrolidone within the stated ranges above.

Preferably, the ratio of the total amount of polyethylene glycol to polyvinylpyrrolidone should be about 20:1.

Propylene Glycol

A component of the present invention is propylene glycol, which is represented by the formula:

is well known in the art for its solvent and/or humectant properties. A colorless and viscous liquid, propylene glycol is miscible with water, alcohols and many organic solvents. Propylene glycol has a bitter taste. Propylene glycol is described in Hawley's Condensed Chemical Dictionary, pp. 970-971, (Revised by Richard J. Lewis, Sr., 12th ed. 1993, herein incorporated by reference). Propylene glycol suitable for use in the present invention is obtainable from any number of suppliers, Dow Chemical being one.

The oral liquid compositions of the present invention comprise from about 1% to about 30% w/v of propylene glycol, more preferably from about 5% to about 20% w/v, and most preferably about 10% w/v of propylene glycol. The process for making the oral liquid compositions of the present invention include the addition of propylene glycol within the stated ranges above.

Pharmaceutical Agents

The compositions of the instant invention contain at least one pharmaceutical agent as an essential component. In general, these pharmaceutical agents have a solubility less than or equal to about 4% w/v in water at 25° C. Useful classes of pharmaceutically-active agents which can be incorporated into the present compositions include analgesics, anti-inflammatory agents, anti-pyretics, calcium channel blockers, beta-blockers, antibacterials, antidepressants, anti-diabetics, anti-emetics, antihistamines, cerebral stimulants, sedatives, antiparasitics, expectorants, diuretics, decongestants, antitussives, muscle relaxants, anti-Parkinsonian agents, bronchodilators, cardiotonics, antibiotics, antivirals, nutritional supplements (such as vitamins, minerals, fatty acids, amino acids, and the like), and mixtures thereof. Pharmaceutical agents selected from the non-narcotic analgesics/nonsteroidal anti-inflammatory drugs are especially useful in the present invention. Examples of such drugs are disclosed in U.S. Pat. No. 4,522,828, to Sunshine et al., issued Jun. 11, 1985, incorporated herein by reference in its entirety.

Examples of preferred pharmaceutical agents useful in the present invention include, but are not limited to, acetaminophen, acetylsalicylic acid, dextromethorphan, ibuprofen, fenbuprofen, fenoprofert, flurbiprofen, guaifenesin, phenylephrine, indomethacin, ketoprofen, naproxen, their pharmaceutically-acceptable salts, and mixtures thereof. Guaifenesin is especially preferred for use in the present invention.

Guaifenesin, which is represented by the formula: $C_{10}H_{14}O$, includes hydrophilic end groups which are soluble in water and hydrophobic end groups which limit water solubility. Guaifenesin may be used in the composition in amounts of about 0.4% w/v to about 6% w/v and preferably in amounts of about 2% w/v to about 4% w/v. Guaifenesin suitable for use in the present invention is obtainable from any number of suppliers, Rhodia Operations SAS of Aubervilliers, France being one.

Guaifenesin, a soluble pharmaceutical agent in water, has a solubility of approximately 4% by weight in water at 25° C. However, it is well known that saturated solutions are prone to precipitate at cold temperatures. Precipitation of guaifenesin out of solution in a concentrated cold and cough oral liquid composition, particularly at low temperatures, is a problem for many manufacturers and distributors. Many consumer complaints regarding the guaifenesin precipitation issue in commercially available compositions led to the research and development of the present invention. Further complicating the issue, ingredient changes to the composition affected the chemical stability of additional pharmaceutical agents in the composition, such as phenylephrine HCl.

Preferably the phenylephrine is in a salt form. Suitable salt forms include, but are not limited to, phenylephrine hydrochloride (HCl), hydrobromide (HBr), bitartarate and tannate salts. Preferably, phenylephrine is used in an amount of about 0.001% w/v to about 2.5% w/v.

Phenylephrine suitable for inclusion in the present invention is available from multiple commercial suppliers, such as Boehringer Ingerheim of Ridgefield, Conn.

Herein percent w/v means a percentage determined by the following formula:

w/v %=Weight of component (in grams)/Volume of composition (in milliliters)×100.

Accordingly, for example, 1% w/v phenylephrine means 1 gram of phenylephrine in 100 ml of the oral liquid composition.

While a liquid composition comprising polyethylene glycol, propylene glycol, polyvinylpyrrolidone, along with guaifenesin and phenylephrine may seem to be a fairly straight forward liquid composition, the interactions between the agents themselves and with additional ingredients complicates the solubility of the agents in the liquid composition, the stability of the agents, and the taste to the consumer.

Polyethylene glycol, particularly PEG™ 400, and propylene glycol assist in the inhibition of the precipitation of guaifenesin but are bitter tasting and contain aldehydic impurities, such as formaldehyde and acetaldehyde, that degrade the phenylephrine.

Polyvinylpyrrolidone is considered a very effective agent for inhibiting precipitation of highly concentrated pharmaceutical agents in liquids and liquid filled soft gels. It is disclosed in U.S. Pat. No. 5,505,961, assigned to R. P. Scherer, that polyvinylpyrrolidone is essential for inhibiting crystallization in liquid-filled soft gel capsules containing high concentrations of acetominophen. PCT Application WO 93/00072, Coapman, discloses a process for solubilizing pharmaceutical actives considered difficult to solubilize. This process requires polyvinylpyrrolidone to aid in solubilizing the active agent and preventing precipitation. Similar limitations are disclosed for the acetaminophen solutions described in PCT Application WO 95/23595, by Dhabhar, wherein polyvinylpyrrolidone is disclosed as an essential component of the compositions that are the subject matter of the Dhabhar patent. However, polyvinylpyrrolidone, while inhibiting the precipitation of guaifenesin, also may contain aldehydic impurities which degrade the phenylephrine. Polyvinylpyrrolidone can also assist in masking the bitter taste of the glycols.

Preferably, the ratio of the total amount of polyvinylpyrrolidone to guaifenesin should be about 1:2 in the absence of phenylephrine in the compositions of the present invention.

In the presence of phenylephrine, the ratio of the total amount of polyvinylpyrrolidone to guaifenesin should be about 1:8 in the compositions of present invention.

Additional Pharmaceutical Agents and Ingredients

An artificial sweetener may be provided to improve palatability. An artificial sweetener is preferred for use as a sweetener to the use of conventional sugar sweeteners as the inventors believe, without wishing to be held to the theory that conventional sugars may contribute to the degradation of phenylephrine in aqueous based compositions. Suitable artificial sweeteners, include but are not limited to, sucralose, saccharine salts, cyclamates, acesulfame K, dipeptide based sweeteners, aspartame and mixtures thereof. Sucralose, which is a high intensity sweetener, is particularly well suited for use in the composition. Sucralose may be used in an amount of about 0.01% to about 0.4% w/v, for example. The appropriate amount of artificial sweetener depends on properties and sweetness intensity of the artificial sweetener and target organoleptic properties of the composition. One skilled in the art is familiar with the characteristics of sweeteners and methods for determining amount of sweetener to be used.

Optionally, glycerin and sorbitol may be used in solution and suspension embodiments of the composition for taste masking. However glycerin and sorbitol contain aldehydic impurities which contribute to the degradation of phenylephrine. In one embodiment the composition contains more glycerin than sorbitol. The inventors believe, without wishing to be bound to the theory, that reduced amounts of sorbitol facilitate stability of the phenylephrine. The composition may contain up to 45% w/v glycerin and up to about 50% w/v sorbitol. In exemplary embodiments with reduced sorbitol amounts, the composition may contain about 18% to about 30% w/v glycerin and about 3% to about 25% w/v sorbitol. Herein the amounts of sorbitol and glycerin are the amounts of standard commercial preparations of sorbitol and glycerin. Commercial sorbitol (as obtained from SPI Polyols, 321 Cherry Lane New Castle, Del. 19720, or Roquette Freves 62080 Lestrew, France, for example) is an aqueous based composition that is 70% sorbitol. Commercial glycerin (as obtained from Dow Chemical Co., 2030 Dow Center, Midland, Mich. 48674, or Lyondell, 1221 McKinney St., Houston, Tex. 77253, for example) is 96 percent glycerin. One skilled in the art is familiar with these commercial preparations and methods of adjusting amounts should a different glycerin preparation (such as, for example, a 99% glycerin) or a different sorbitol preparation be used.

The composition may contain one or more additional pharmaceutical agents (also referred to as "active(s)", "active agent(s)", "agents", "therapeutic agent(s)", "drug(s)"). Further, the term pharmaceutical agent may refer to a single species of agent or a plurality of species of agents (e.g., the total number of agents in the compositions may be greater than 3). For embodiments of the composition that are solutions, any additional agent should be water soluble. A water-soluble pharmaceutical agent means a pharmaceutical agent indicated to be soluble in water by the Merck Index. Additional agents in suspension embodiments may be water soluble, slightly soluble in water, or insoluble in an aqueous medium.

Suitable additional pharmaceutical agents include analgesics, decongestants, expectorants, anti-tussives, antipyretics, anti-inflammatory agents, cough suppressants and antihistamines.

Antihistamines useful in the practice of the present invention (along with their preferred salt form) include, but are not limited to, chlorpheniramine (maleate), brompheniramine (maleate); dexchlorpheniramine (maleate), dexbrompheniramine (maleate), triprolidine (HCl), diphenhydramine (HCl, citrate), doxylamine (succinate), tripelenamine (HCl), cyproheptatine (HCl), chlorcyclizine (HCl), bromodiphenhydramine (HCl), phenindamine(tartrate), pyrilamine (maleate, tannate), azatadine (maleate); acrivastine, astemizole, azelastine, cetirizine, ebastine, fexofenadine, ketotifen, carbinoxamine (maleate), desloratadine, loratadine, pheniramine maleate, thonzylamine (HCl), mizolastine and terfenadine.

Antitussives useful in the practice of the present invention (along with their preferred salt form) include, but are not limited to, chlophendianol, caramiphen (ediylate), dextromethorphan (HBr), diphenhydramine (citrate, HCl), codeine (phosphate, sulfate) and hydrocodone.

Decongestants useful in the practice of the invention (along with their preferred salt form) include, but are not limited to, pseudoephedrine (HCl, sulfate), ephedrine (HCl, sulfate), phenylephrine (bitartarate, tannate, HBr, HCl), and phenylpropenolamine (HCl).

Expectorants which may be used in the practice of the invention (along with their preferred salt form) include but are not limited to terpin hydrate, guaifenesin (glycerol, guaiacolate), potassium (iodide, citrate) and potassium guaicolsulfonate.

Non-steroidal anti-inflammatory drugs (NSAIDS) which may be used in the practice of the invention include, but are not limited to, propionic acid derivatives such as ibuprofen, naproxen, ketoprofen, flurbiprofen, fenoprofen, suprofen, fluprofen and fenbufen; acetic acid derivatives such as tolmetin sodium, zomepirac, sulindac, and indomethacin; fenamic acid derivatives such as mefenamic acid and meclofenamate sodium; biphenyl carboxylic acid derivatives such as diflunisal and flufenisal and oxicams such as piroxicam, sudoxicam and isoxicam.

Cox 2 inhibitors which may be used in the practice of the invention include, but are not limited to, celecoxib, rofecoxib and valdecoxib.

Analgesics which may be used in the practice of the invention include but are not limited to aspirin, acetominophen, phenacetin and salicylate salts.

Examples of substantially insoluble pharmaceutical agents that may be suspended in the suspending system of suspension embodiments include, but are not limited to, nabumetone, glimepiride, diclofenac, piroxicam and meloxican.

Of the pharmaceutically agent compounds described above which may be included in addition to guaifenesin and phenylephrine in the composition, those which are particularly preferred are set forth below along with preferred ranges for their inclusion into the claimed pharmaceutical composition.

Chlorpheniramine may be used in the pharmaceutical composition in amounts between about 0.01% w/v and about 0.05% w/v. Preferably chlorpheniramine, when used in the pharmaceutical composition, is present in the amount of about 0.01% w/v to 0.03% w/v.

Chlorpheniramine maleate may be used in the pharmaceutical composition, preferably in the amount of about 0.01% w/v to about 0.03% w/v.

Brompheniramine maleate may be used in the pharmaceutical composition, preferably in the amount of about 0.01% w/v to about 0.03% w/v.

Dextromethorphan HBr may be used in the pharmaceutical composition, preferably in the amount of about 0.05% w/v to about 0.250% w/v.

Chlophendianol may be used in the composition in amounts of about 0.1% w/v to about 1% w/v and preferably in amounts of about 0.25% w/v to about 0.5% w/v.

Diphenhydramine may be used in the composition in amounts of about 0.2% w/v to about 2% w/v and preferably in amounts of about 0.5% w/v to about 1% w/v.

Brompheniramine may be used in the composition in amounts of about 0.016% w/v to about 0.16% w/v and preferably in amounts of about 0.02% w/v to about 0.08% w/v.

Loratadine may be used in the composition in amounts of about 0.02% w/v to about 0.4% w/v and preferably in amounts of about 0.1% w/v to about 0.2% w/v.

Aspirin may be used in the composition in amounts of about 0.8% w/v to about 13% w/v and preferably in amounts of about 3.2% w/v to about 7.2% w/v.

Doxylamine may be used in the composition in amounts of about 0.1% w/v to about 1% w/v and preferably in amounts about 0.25% w/v to about 0.5% w/v.

Acetaminophen may be used in the composition in amounts of about 0.12% w/v to about 13% w/v and preferably in amounts of about 1.2% w/v to about 4% w/v.

Amounts of pharmaceutically agent compounds incorporated are conventional dosages known to those skilled in the art. Further, for pharmaceutical compositions intended for use in the United States, amounts of pharmaceutical agents are preferably in compliance with applicable FDA regulations regarding dosage of such compounds.

The pharmaceutically agent compounds are preferably, but not limited to, a compendial grade such as, for example, N.F. (National Formulary) or U.S.P. (United States Pharmacopeia) grade.

Excipients known by those skilled in the art may be useful in the practice of the present invention. Such excipients may include, but are not limited to, humectants such as glycerin, sweeteners, defoaming agents, buffers, electrolytes, preservatives such as sodium benzoate and disodium edetate, antioxidants, taste masking agents and various flavoring and coloring agents, for example. Optionally, some embodiments may include viscosity modifiers such as, for example, glycerin, xanthan, and/or povidone; and/or densifiers such as, for example, sorbitol or glycerin.

Examples of suitable flavoring agents include, but are not limited to, natural and artificial flavors such as mints (i.e., peppermint, etc.), menthol, chocolate, artificial chocolate, bubblegum, both artificial and natural fruit flavors (i.e., cherry, grape, orange, strawberry, etc.) and combinations of two or more thereof. It is preferable to avoid flavoring agents which have aldehyde functional groups (e.g. use non-aldehyde containing flavorants is preferred). Flavoring agents are generally provided as a minor component of the composition in amounts effective to provide palatable flavor to the compositions. Typically, flavoring agents are present in amounts in the range of about 0% w/v to about 5% w/v in the composition.

Optionally, an antioxidant may be used in the composition. Propyl gallate is exemplary of an antioxidant that is suitable for use in the composition.

Preservatives useful in the present invention include but are not limited to sodium benzoate, sorbates, such as potassium sorbate, salts of edetate (also known as salts of ethylenediaminetetraacetic acid or EDTA, such as disodium edetate), benzaldionium chloride and parabens (such as methyl, ethyl, propyl, and butyl p-hydroxybenzoic acid esters). Preservatives listed above are exemplary, but each preservative must be evaluated on an experimental basis, in each formulation to assure compatibility and efficacy of the preservative. Methods for evaluating the efficacy of preservatives in pharmaceutical formulations are known to those skilled in the art. Sodium benzoate and disodium edetate are the presently preferred preservative ingredients.

Preservatives are generally present in amounts of up to one gram per 100 ml of the pharmaceutical composition. Preferably the preservatives are present in amounts in the range of from about 0.01% w/v to about 0.4% w/v of the composition. Typically, the preservative sodium benzoate would be present in the range of about 0.1% w/v to about 0.2% w/v of the composition, for example. Sodium benzoate was used in a concentration of about 0.1% w/v in an exemplary embodiment of the composition.

Sodium citrate is exemplary of a buffering agent which may be used in the composition. It is preferable to buffer the composition to maintain the pH in the range from about pH 2 to about pH 5. More preferably, the pH is maintained in the range from about 3.2 to about 3.8. Most preferably, the pH is about 3.5.

Coloring agents may also be incorporated in the pharmaceutical composition to provide an appealing color to the composition. The coloring agents should be selected to avoid chemical incompatibilities with other ingredients in the composition. Suitable coloring agents are well known to those skilled in the art.

In some embodiments, particularly suspension embodiments, a surface modifying agent, such as a surfactant, may be used in the pharmaceutical composition to modify the surface of the suspended components. Such surface modification is believed to facilitate diminished irreversible aggregation of the suspended particles. The surfactant may be an ionic or non-ionic surfactant or mixtures thereof. Exemplary surfactants include but are not limited to polysorbates (tweens), Span™, togats, lecithin, polyoxyethylene-polyoxypropylene block copolymers and medium chain mono/di-glycerides.

Typically, suspension embodiments will further comprise a viscosity modifying agents. Suitable viscosity modifying agents include but are not limited to chitosan, xanthan, povidone, hydroxpropylmethylcellulose (HPMC), hydroxypropylcellulose (HPC), hydroxyethylcellulose (HEC), glactomannons such as guar, konjac, locust bean gum and mamman, for example, microcrystalline cellulose and combinations thereof.

Xanthan gums suitable for use in the present invention are high molecular weight polysaccharides such as the xanthan gum produced by *Xanthamonas capestris*, for example. Xanthan gum is an article of commerce and is available, for example, from manufacturers such as: Rhodia, Inc. under the brand name Rhodigel™ and from Kelco™, a division of Merck. Rhodigel™ 80 Pharm Grade is exemplary of one specific commercial product suitable for use in the practice of the invention.

Microcrystalline cellulose is commercially available from suppliers such as FMC (1735 Market Street, Philadelphia, Pa. 19103) under the tradename AvicelV™.

The amount of viscosity modifier used depends on the desired "thickness" of the composition and the type viscosity modifier used. Combinations of viscosity modifiers may be employed. For example, in an exemplary embodiment with a viscosity of about 1500 to about 4500 cps, up to about 1.0% w/v xanthan gum may be used and up to about 3.0% w/v microcrystalline cellulose may be used as a viscosity modifier.

It is preferable to avoid viscosity modifiers with a significant presence of negatively charged moieties or moieties with propensity to ionize to a negative charge if the structure of the modifier is such that the negatively charged moiety is readily available for reaction.

Suspensions are useful for preparing compositions comprising agents that are substantially insoluble in water. In suspension embodiments the phenylephrine is dissolved in the aqueous medium. The composition may contain one or more second agent agents dissolved in the aqueous medium and/or one or more substantially water insoluble second agent agents may be suspended in the composition. For the suspension embodiments, it is preferable that both the suspended substantially insoluble agent ingredients and any soluble agent ingredients dissolved in the aqueous medium, are distributed to form a substantially homogeneous distribution of agent ingredients in the pharmaceutical composition.

Exemplary pharmaceutical agents that are substantially insoluble in the aqueous composition and would be expected to form suspension include but are not limited to ibuprofen, ketoprofen, naproxen, celecoxib, rofecoxib, valdecoxib, nabumetone, glimepiride, diclofenac, piroxicam and meloxican. For pharmaceutical agents not specified on this list a pharmaceutical agent substantially insoluble in the aqueous composition means a pharmaceutical agent designated as relatively insoluble or insoluble in water by the Merck Index.

Typically, solution and suspension forms of the composition are provided to a patient in need of treatment in a dosage unit of 10 mL although other dosage units may be likewise suitable. The dosage unit may be provided as a single dosage unit or multiples thereof, based on age, weight and other health parameters determined by a physician to be relevant.

Soft Gelatin Capsules

The solubilized pharmaceutical compositions of the present invention can be encapsulated within any conventional soft gelatin shell that is capable of substantially containing the composition for a reasonable period of time. Optionally, the soft gelatin shell is essentially transparent so as to enhance the aesthetic qualities of the capsule. The soft gelatin shells may comprise well known essential components, such as gelatin, plasticizer and water as well as optional components such as described in U.S. Pat. No. 5,484,606, issued to Dhabhar on Jun. 16, 1996, herein incorporated by reference in its entirety.

Solubility

Because the resultant concentrated oral liquid composition (or fill) is a saturated solution of the soluble pharmaceutical agent(s), there is a tendency for the dissolved soluble pharmaceutical agent(s) to precipitate out of solution, particularly at lower temperatures, such as 4° C. and below.

Several approaches to solve the issues of guaifenesin precipitation and the reduced stability of phenylephrine HCl were undertaken, but failed to cure the problems.

Viscosity modifications were explored but the resultant compositions with improved cold temperature stability could not be considered viable commercial compositions due to their unpalatable viscosity.

Several materials for use as precipitation inhibitors were considered, including two grades of poloxamer and several grades of polyvinylpyrrolidone. However, published prior art, such as literature and patents, teaches away from using polyvinylpyrrolidone with phenylephrine because polyvinylpyrrolidone comprises acetaldehyde as a byproduct of the manufacture. Aldehydes, especially formaldehyde and acetaldehyde, are known to react with phenylephrine HCl and degrade the stability of phenylephrine HCl. Formaldehyde is also present in polyvinylpyrrolidone and polyethylene glycol. The major phenylephrine degradants are formed by reactions with aldehydes. Specifically, phenylephrine reacts with formaldehyde and acetaldehyde to form isoquinoline compounds.

A pre-formulation tri-modal solubility experiment to determine the preferred concentrations of polyethylene glycol, propylene glycol to inhibit the guaifenesin precipitation was performed using various levels of co-solvents, such as polyethylene glycol, propylene glycol, and ethanol. For the present invention, ethanol is not a preferred ingredient due to manufacturing and commercial marketing purposes and thus the ethanol experiments were terminated. It was discovered that preferred concentrations of propylene glycol and polyethylene glycol to be from about 5% w/v to about 20% w/v each, more preferably about 10% to about 15% w/v each. Thus, additional formulation work was necessary, including the use of glycerin and polyvinylpyrrolidone. Glycerin did not assist in solubilization of guaifenesin but the addition of polyvinylpyrrolidone assisted in inhibiting the precipitation of guaifenesin in cold temperatures (4° C. and −20° C.), as shown in Examples below. Applicants then proceed to conduct experimentation on the compositions for both solubility and stability in the Examples below.

Once the guaifenesin solubility issues, the next issue was the chemical stability of the phenylephrine HCl. A cation exchange high performance liquid chromatography (HPLC) assay was used for analytical calculation of the % phenylephrine HCl, and the total unspecified degradants related to phenylephrine HCl. Table 2 comprises the average value calculated from data points collected from each sample composition tested. The respective data points are disclosed in the Examples below.

Due to storage, shipping and other commercial demands, stability and solubility time periods should be as long as possible, preferably at least 12 days, more preferably at least 14 days.

The term "visible" in the present invention means observable, detectable, or able to be seen by the naked eye. The term "visibly free" in the present invention means not observable, not detectable, or unseen by the naked eye.

Although Composition 2 had the longest time period of 22 days with no visible guaifenesin precipitation (see Table 1), the average amount of phenylephrine degradants was higher than the other compositions (see Table 2). The amount of phenylephrine degradants was observed to increase when the concentration of polyvinylpyrrolidone was increased (see Table 2).

Customary industry acceptable levels of phenylephrine degradants are about 8%. Levels of phenylephrine HCl degradation were observed in the 2% w/v polyvinylpyrrolidone prototypes (Composition 2 in Example 2), as discussed below and exemplified in Table 2. Given that the amount of impurities in the raw material is variable, Applicants decided to formulate the product with the least amount of polyvinylpyrrolidone to avoid negative impact on the phenylephrine HCl stability. Various levels of polyvinylpyrrolidone were experimented with, ranging from about 0% to about 4% w/v. After much experimentation, the preferred concentration of polyvinylpyrrolidone was determined to be about 0.5% w/v.

Composition 4, comprising about 0.5% w/v polyvinylpyrrolidone, about 10% w/v polyethylene glycol and about 10% w/v propylene glycol, remained physically stable, (e.g. all agents remain in solution) for at least 62 days at 4° C. and for 14 days at −20° C. Composition 4 in Table 1 met the highly preferred 2-week stability minimum sought by commercial standards.

Processes

Manufacturing difficulties arise when adding large amounts of pharmaceutical agent(s) and polyvinylpyrrolidone to an aqueous solution. Applicants' innovative approach was implemented using an inline high-shear mixer, preferably a Silverson Flashbend™ (FLB30).

The compositions of the present invention are prepared by simple mixing. The ingredients are mixed in a vessel equipped with a mechanical stirrer (e.g., a Lightnin mixer), the vessel calibrated and marked to designate the final volume. The polyvinylpyrrolidone, preferably Povidone™ K-90, was initially dispersed through an inline high shear mixer (Silverson Flashbend™ (FLB30)) into the vessel with a predetermined amount of water. The guaifenesin was then added and dissolved in the solution, followed by an aliquot of water substantially less than the target final volume. The propylene glycol is added next with mixing, and then the polyethylene glycol is added with mixing. The additional ingredients are added either sequentially or pre-mixed with other ingredients and then added under manufacturing processes well known in the medicinal liquid medication art.

Uniform mixing is determined by well known standards, such as stabilized refractive index monitoring system. Colorants may be added directly or premixed with a small amount of water prior to addition to the main vessel. After all other ingredients are added and mixed sufficiently to dissolve, water is added to bring the total volume of the composition to the predetermined final volume and mixing is continued for approximately thirty minutes for a total mixing time of about 4 hours.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention.

Sample compositions were placed in a refrigerator (4° C.) and a freezer (−20° C.) and monitored for visible precipitation once per day. Table 1 illustrates the number of days with no visible precipitation of guaifenesin for the present compositions or, in other words, wherein the compositions are visually free of guaifenesin precipitation at 4° C. and at −20° C.

The following examples illustrate the effect of the interaction between guaifenesin, phenylephrine, and the various amounts of polyvinylpyrrolidone. Variability of impurities in the agents and ingredients used in the different compositions were not analyzed.

Example 1

Composition 1 comprises 0% w/v polyvinylpyrrolidone, about 10% w/v polyethylene glycol and about 10% w/v propylene glycol. Guaifenesin precipitation was not visible to the naked eye for at 11 days at −20° C. and for 50 days at 4° C. (See Table 1).

Chemical stability tests to determine the degradation of phenylephrine were not conducted on Composition 1.

| Composition 1 | Amount (% w/v) |
| --- | --- |
| Dextromethorphan HBr | 0.20% |
| Guaifenesin | 4.00% |
| Phenylephrine HCl | 0.10% |
| Propylene Glycol | 10.00% |
| Polyethylene Glycol | 10.00% |
| Polyvinylpyrrolidone (K-90) | 0.00% |
| Citric Acid | 0.90% |
| Xanthum Gum | 0.10% |
| Menthol | 0.02% |
| Glycerin | 24.07% |
| FD&C Red #40 | 0.01% |
| Flavorant | 0.80% |
| Sodium Benzoate | 0.10% |
| Sodium Citrate | 0.20% |
| Sorbitol | 20.00% |
| Sucralose | 0.20% |
| Water | q.s. |

"q.s." is an abbreviation for the Latin term "quantum satis" or "sufficient quantity"

Method

Composition 1 is prepared by simple mixing. The ingredients are mixed in a vessel equipped with a mechanical stirrer (e.g., a Lightnin mixer), the vessel calibrated and marked to designate the final volume. A predetermined amount of water is added into the vessel. The guaifenesin is then added and dissolved in the solution, followed by an aliquot of water substantially less than the target final volume. The propylene glycol is added next with mixing, and then the polyethylene glycol is added with mixing. The additional ingredients are added either sequentially or pre-mixed with other ingredients and then added under manufacturing processes well known in the medicinal liquid medication art. Uniform mixing is determined by well known standards, such as stabilized refractive index monitoring system. Colorants may be added directly or premixed with a small amount of water prior to addition to the main vessel. After all other ingredients are added and mixed sufficiently to dissolve, water is added to bring the total volume of the composition to the predetermined final volume and mixing is continued for approximately 2 hours.

Example 2

Composition 2 comprises about 2% w/v polyvinylpyrrolidone, about 10% w/v polyethylene glycol and about 10% w/v propylene glycol. Guaifenesin precipitation was not visible to the naked eye for about 22 days at −20° C. and for at least 62 days at 4° C. Applicants terminated their visual inspection after 62 days.

Applicants conducted two stability tests over a 3 month time period at 40° C. and 75% relative humidity on two identically prepared developmental samples of Composition 2. As shown in Table 2, the average degradation of the phenylephrine was observed to be about 3% total unspecified phenylephrine degradants, calculated from data in a range from about 1.97% to about 4.11%, and about 6% loss of phenylephrine, calculated from data in a range from about 5.28% to about 7.20% (see Composition 2 in Table 2).

| Composition 2 | Amount (% w/v) |
| --- | --- |
| Dextromethorphan HBr | 0.20% |
| Guaifenesin | 4.00% |
| Phenylephrine HCl | 0.10% |
| Propylene Glycol | 10.00% |
| Polyethylene Glycol | 10.00% |
| Polyvinylpyrrolidone (K-90) | 2.00% |
| Citric Acid | 0.90% |
| Xanthum Gum | 0.10% |
| Menthol | 0.02% |
| Glycerin | 24.07% |
| FD&C Red #40 | 0.01% |
| Flavorant | 0.80% |
| Sodium Benzoate | 0.10% |
| Sodium Citrate | 0.20% |
| Sorbitol | 20.00% |
| Sucralose | 0.20% |
| Water | q.s. |

Composition 2 is prepared by simple mixing. The ingredients are mixed in a vessel equipped with a mechanical stirrer (e.g., a Lightnin mixer), the vessel calibrated and marked to designate the final volume. The polyvinylpyrrolidone was initially poured through an inline high shear mixer into the vessel with a predetermined amount of water. The guaifenesin was then added and dissolved in the solution, followed by an aliquot of water substantially less than the target final volume. The propylene glycol was added next with mixing, and then the polyethylene glycol with mixing. The other ingredients are added sequentially with mixing. Colorants may be added directly or premixed with a small amount of water prior to addition to the main vessel. After all other ingredients are added and mixed sufficiently to dissolve, water is added to bring the total volume of the composition to the predetermined final volume and mixing is continued for approximately 2 hours.

Example 3

Composition 3 comprises about 1% w/v polyvinylpyrrolidone, about 10% w/v polyethylene glycol and about 10% w/v propylene glycol. Guaifenesin precipitation was not visible to the naked eye for about 14 days at −20° C. and about 45 days at 4° C. Applicants terminated their visual inspection after 45 days.

Applicants conducted two stability tests over a 3 month time period at 40° C. and 75% relative humidity on two identically prepared samples of Composition 3. As shown in Table 2, the average degradation of the phenylephrine was observed to be about 2.27% total unspecified phenylephrine degradants, calculated from data in a range from about 1.99% to about 2.55%, and about 5% loss of phenylephrine, calculated from data in a range from about 4.8% to about 5.2% (see Composition 3 in Table 2).

| Composition 3 | Amount (% w/v) |
|---|---|
| Dextromethorphan HBr | 0.20% |
| Guaifenesin | 4.00% |
| Phenylephrine HCl | 0.10% |
| Propylene Glycol | 10.00% |
| Polyethylene Glycol | 10.00% |
| Polyvinylpyrrolidone (K-90) | 1.00% |
| Citric Acid | 0.90% |
| Xanthum Gum | 0.10% |
| Menthol | 0.02% |
| Glycerin | 24.07% |
| FD&C Red #40 | 0.01% |
| Flavorant | 0.80% |
| Sodium Benzoate | 0.10% |
| Sodium Citrate | 0.20% |
| Sorbitol | 20.00% |
| Sucralose | 0.20% |
| Water | q.s. |

Composition 3 may be prepared using the manner of preparation described in Example 2.

Example 4

Composition 4 comprises about 0.5% w/v polyvinylpyrrolidone, about 10% w/v polyethylene glycol and about 10% w/v propylene glycol. Guaifenesin precipitation was not visible to the naked eye for about 14 days at −20° C. and for at least 62 days at 4° C.

The composition is visually free of guaifenesin precipitation for at least 62 days at 4° C. and the composition is visually free of guaifenesin precipitation for 14 days at −20° C. Applicants terminated their visual inspection after 62 days. After Applicants observed visible precipitation on the 14th day in the sample composition at −20° C., Applicants removed the sample composition from the freezer and allowed the sample composition to warm to room temperature (22° C.). Applicants visually observed that all the precipitation in the sample composition solubilized back into the solution within 24 hours. No further visual observations were conducted on the sample composition.

Applicants conducted three stability tests over a 3 month time period at 40° C. and 75% relative humidity on three identically prepared samples of Composition 4. As shown in Table 2, the average degradation of the phenylephrine was observed to be about less than 2% total unspecified phenylephrine degradants, calculated from data in a range from about 1.59% to about 1.76%, and an average of less than 2% loss of phenylephrine, more specifically an average of about 1.3% loss of phenylephrine, calculated from data in a range from about 0.73% to about 1.94% (see Composition 4, Table 2).

| Composition 4 | Amount (% w/v) |
|---|---|
| Dextromethorphan HBr | 0.20% |
| Guaifenesin | 4.00% |
| Phenylephrine HCl | 0.10% |
| Propylene Glycol | 10.00% |
| Polyethylene Glycol | 10.00% |
| Polyvinylpyrrolidone (K-90) | 0.50% |
| Citric Acid | 0.90% |
| Xanthum Gum | 0.10% |
| Menthol | 0.02% |
| Glycerin | 24.07% |
| FD&C Red #40 | 0.01% |
| Flavorant | 0.80% |
| Sodium Benzoate | 0.10% |
| Sodium Citrate | 0.20% |
| Sorbitol | 20.00% |
| Sucralose | 0.20% |
| Water | q.s. |

Composition 4 may be prepared using the manner of preparation described in Example 2.

TABLE 1

Number of days with no observed precipitation of guaifenesin at 4° C. and at −20° C.

| Composition # (% PVP) | Number of days with no observed precipitation at −20° C. | Number of days with no observed precipitation at 4° C. |
|---|---|---|
| Composition 1 (0%) | 11 | 50 |
| Composition 2 (2%) | 22 | 62+ |
| Composition 3 (1%) | 14 | 45+ |
| Composition 4 (0.5%) | 14 | 62+ |

Sample compositions were placed in a refrigerator (4° C.) or a freezer (20° C.) and monitored for precipitation once per day. Guaifenesin precipitation was not visible to the naked eye until the number of days stated in Table 1 above.

TABLE 2

| Composition # | Time at 40° C./75% RH (months) | Average Total unspecified phenylephrine (PE) degradants | Average Loss of PE (% Initial-% at 3 months) |
|---|---|---|---|
| 1 | Not tested | Not tested | Not tested |
| 2 | 3 | about 3% | about 6% |
| 3 | 3 | about 2% | about 5% |
| 4 | 3 | about less than 2% | about less than 2% |

RH = relative humidity
% initial = % of phenylephrine (PE) present at initial testing of newly mixed composition
% at 3 months = % of phenylephrine (PE) present three months after initial testing of newly mixed composition Although the foregoing invention has been described in some detail by way of illustrations and examples for purposes of clarity of understanding. It will be obvious that certain changes and modifications may be practiced within the scope of the appended claims. Modifications of the above-described modes of practicing the invention that are obvious to persons of skill in the art are intended to be included within the scope of the following claims.

The invention claimed is:
1. A liquid oral pharmaceutical composition comprising:
   i.) from about 0.1% to about 20% w/v polyvinylpyrrolidone;
   ii.) from about 5% to about 70% w/v polyethylene glycol;

iii.) from about 1% to about 30% w/v propylene glycol;
iv.) from about 1% to 10% w/v guaifenesin; and
v.) from about 0.01% to about 1.0% w/v phenylephrine
wherein the composition is visually free of guaifenesin precipitation for at least 62 days at 4° C.

2. A liquid oral pharmaceutical composition comprising:
i.) from about 0.1% to about 20% w/v polyvinylpyrrolidone;
ii.) from about 5% to about 70% w/v polyethylene glycol;
iii.) from about 1% to about 30% w/v propylene glycol;
iv.) from about 1% to 10% w/v guaifenesin; and
v.) from about 0.01% to about 1.0% w/v phenylephrine,
further comprising about 4% w/v guaifenesin and about 0.10% w/v phenylephrine, wherein the composition is visually free of guaifenesin precipitation for 14 days at −20° C.

3. A liquid oral pharmaceutical composition comprising:
i.) from about 0.1% to about 20% w/v polyvinylpyrrolidone;
ii.) from about 5% to about 70% w/v polyethylene glycol;
iii.) from about 1% to about 30% w/v propylene glycol;
iv.) from about 1% to 10% w/v guaifenesin; and
v.) from about 0.01% to about 1.0% w/v phenylephrine,
wherein the composition comprises about 4% w/v guaifenesin and about 0.10% w/v phenylephrine, about less than 2% total phenylephrine degradants, as a percent weight over weight phenylephrine, and about less than 2% loss of phenylephrine from the initial total phenylephrine content, measured over a 3 month time period while stored at 40° C. and 75% relative humidity.

4. A process for preparing an oral liquid composition, comprising the steps of:
a.) mixing until dissolved from about 0.1% to about 20% w/v of polyvinylpyrrolidone in an aqueous phase;
b.) adding and mixing from about 1% to about 20% w/v of at least one pharmaceutical agent;
c.) subsequently adding and mixing:
i.) water;
ii.) from about 1% to about 30% w/v of a propylene glycol;
iii.) from about 5% to about 70% w/v of a polyethylene glycol; and
d.) subsequently adding and mixing one or more additional ingredients.

5. The process of claim 4 wherein the composition comprises about less than 2% total phenylephrine degradants, as a percent weight over weight phenylephrine, and about less than 2% loss of phenylephrine from the initial total phenylephrine content, measured over a 3 month time period while stored at 40° C. and 75% relative humidity.

6. The process of claim 4, wherein the composition is visually free of guaifenesin precipitation for at least 62 days at 4° C.

* * * * *